United States Patent [19]

Russo et al.

[11] 4,317,452

[45] Mar. 2, 1982

[54] BODY FLUID DRAIN

[75] Inventors: Ronald D. Russo, Barrington; Francis E. Blinkhorn, North Kingstown; Len L. Curado, East Greenwich, all of R.I.

[73] Assignee: C. R. Bard, Inc., Murray Hill, N.J.

[21] Appl. No.: 118,550

[22] Filed: Feb. 4, 1980

[51] Int. Cl.³ .............................................. A61M 1/00
[52] U.S. Cl. ................................................. 128/350 R
[58] Field of Search ......................... 128/350 R, 350 V

[56] References Cited

U.S. PATENT DOCUMENTS

| | | | |
|---|---|---|---|
| 1,596,754 | 8/1926 | Moschelle | 128/350 |
| 1,928,992 | 10/1933 | Clark et al. | 128/350 X |
| 3,310,051 | 3/1967 | Schulte | 128/350 |
| 3,314,430 | 4/1967 | Alley et al. | 128/350 |
| 3,399,668 | 9/1968 | Lundgren | 128/350 X |
| 3,430,631 | 3/1969 | Abramson | 128/350 |
| 3,459,189 | 8/1969 | Alley et al. | 128/347 |
| 3,495,595 | 2/1970 | Soper | 128/350 |
| 3,595,241 | 7/1971 | Sheridan | 128/350 |
| 3,630,207 | 12/1971 | Kahn | 128/350 |
| 3,805,794 | 4/1974 | Schlesinger | 128/349 |
| 3,885,561 | 5/1975 | Cami | 128/214 |
| 3,957,054 | 5/1976 | McFarlane | 128/350 |
| 4,257,422 | 3/1981 | Duncan | 128/350 R |

OTHER PUBLICATIONS

Jackson, Frederick, Jackson-Pratt Brain Drain, Surgical Technics, 2/18/72.
Hendrickson Suprapubic Drain, ACMI Catalogue, 1938.

*Primary Examiner*—Robert W. Michell
*Assistant Examiner*—Nancy A. B. Swisher
*Attorney, Agent, or Firm*—Robert R. Jackson; Charles B. Smith

[57] ABSTRACT

A flexible body fluid drain tube has substantially flat cross section with a pair of parallel longitudinal internal ribs along one substantially flat wall which are spaced apart a distance greater than their respective distances from the adjacent edges of the flat wall, a central internal longitudinal rib along the opposite substantially flat wall, and a pattern of drain holes along both flat walls in line with the parallel ribs. The ribs prevent the tube from collapsing even when the tube is subject to a very high vacuum and/or strong lateral compression forces due to body movements of the patient and the healing process at the drainage site. The central rib can wipe back and forth across the opposite wall to keep the tube passageway and drain holes clear when the flat tube walls are moved laterally relative to one another by body movements of the patient and the healing process.

9 Claims, 12 Drawing Figures

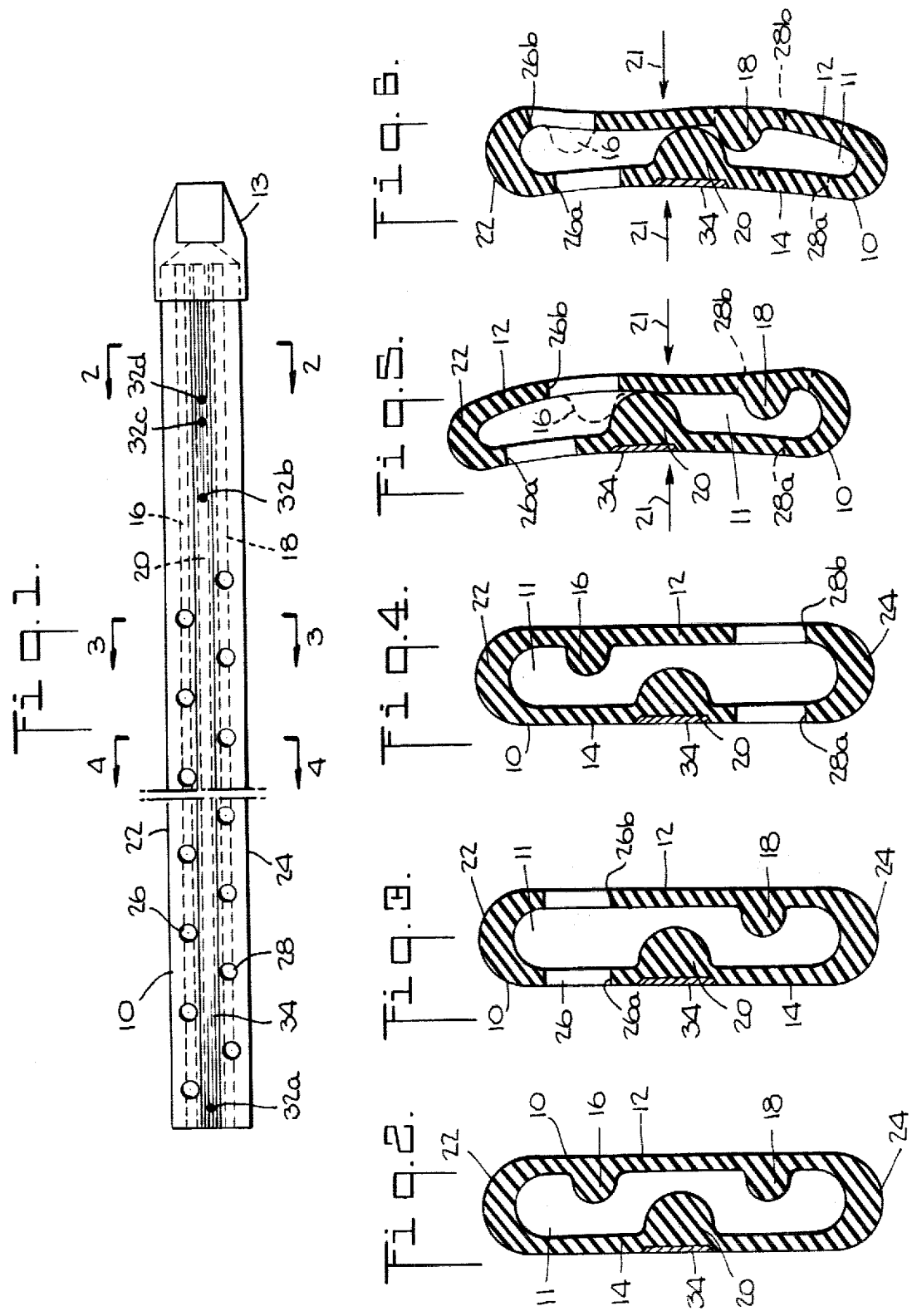

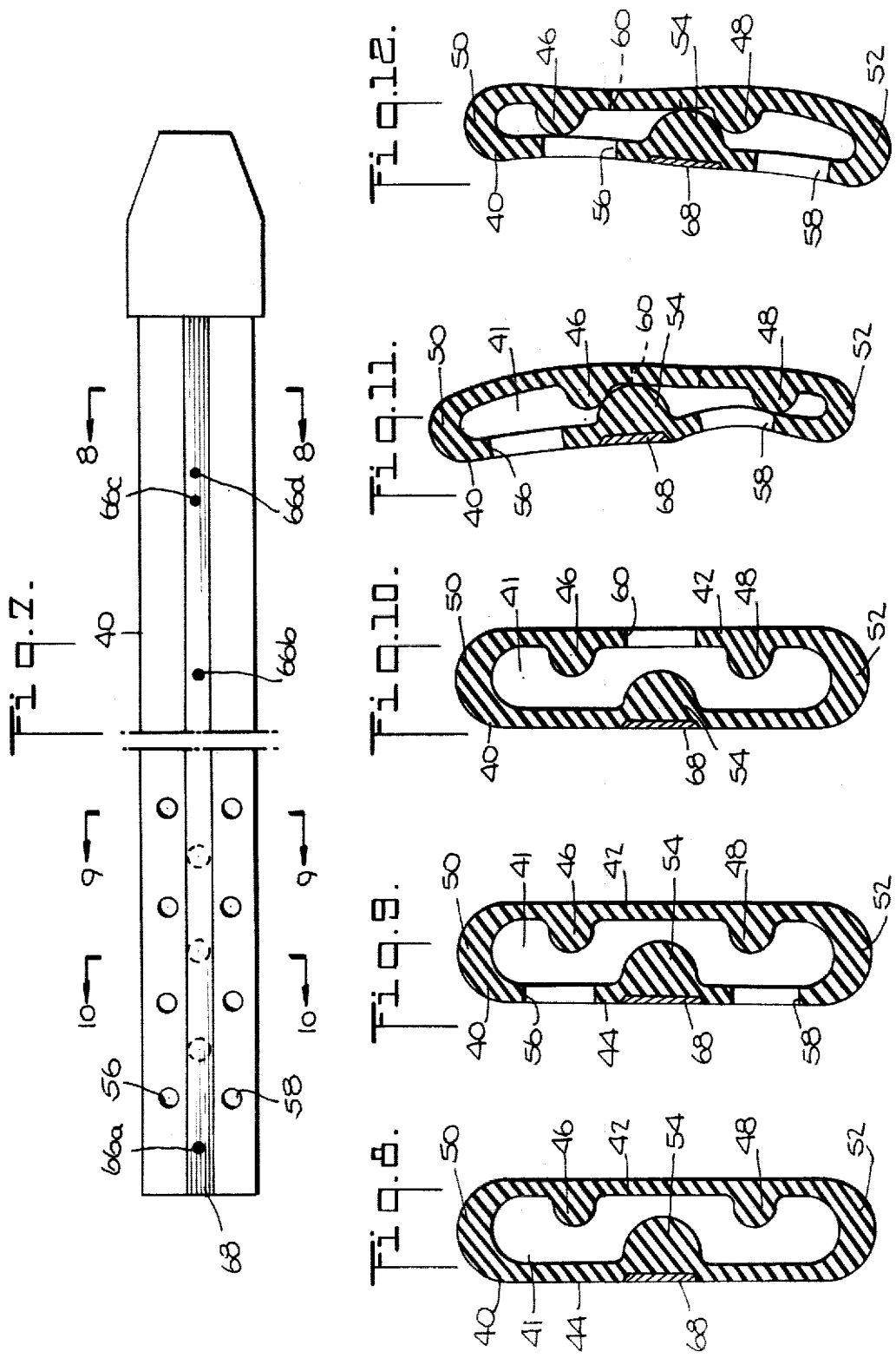

BODY FLUID DRAIN

BACKGROUND OF THE INVENTION

Body fluid drains are used at so-called drainage sites for draining fluids from cavities in a patient's body, usually during and after surgical procedures. The drainage site may be a natural body cavity or orifice or may be surgically formed. The attainment of a balance of good operative and functional properties in such fluid drains has been a continuing developmental problem. For instance, a tube having a round cross section formed of a rigid material such as metal or plastic will remain open and non-collapsible so that its passageway will generally stay clear. But such rigid drainage devices have long been considered unsatisfactory by surgeons because of the danger of trauma to the tissues and surrounding organs into which they are inserted caused by the non-yieldability of the drainage tube during the patient's body movements.

On the other hand, when drainage tubes are made of a soft yieldable material, they tend to collapse when significant vacuum or suction pressure is applied to them, as is required in many applications, or when the patient's normal body movements or the healing process cause compressive pressures on them.

Several forms of drainage tubes have been developed from soft yieldable materials with internal ribbing and other configurations of stiffening elements to prevent closure and stoppage of the drainage function resulting from collapse during use.

However, the medical profession is still not entirely satisfied with existing drainage tubes and is anxious to have available improved and more foolproof drain tubes. The problem has become more acute since it has also been found desirable to have such drainage devices made from the newer, softer, smoother and more yieldable and flexible materials such as silicone rubber which, when formed as a tube, has an even greater tendency to collapse and create drainage stoppages under normal functional compressive forces.

It is accordingly an object of this invention to provide drainage tubes for body fluids which can be made of the softest and most yieldable materials available such as silicone rubber and which at the same time will continue to function by maintaining a clear drainage passageway to the exterior of the drainage site even when subjected to compressive forces caused by suction pressure applied to the tube and/or by the patient's body movements and the healing process.

SUMMARY OF THE INVENTION

This and other objects of the invention are accomplished in accordance with the principles of the invention by providing drainage tubes made of a soft yieldable material, preferably silicone rubber, which have a substantially flat cross section with relatively thin, relatively wide opposite first and second walls spaced apart by a distance substantially less than their width. The adjacent lateral edges of the first and second walls are joined by further wall portions which are preferably somewhat thicker than the first and second walls. A pair of parallel, laterally spaced, longitudinal ribs extend along the inside of the first wall. Another longitudinal rib extends along the inside of the second wall and projects into the interior of the tube intermediate the pair of ribs on the first wall. The ribs on the first wall are spaced apart a distance greater than the width of the rib on the second wall. The spacing between the ribs on the first wall is also preferably greater than the distance from each rib to the adjacent edge of the first wall. Each rib is preferably substantially wider and thicker than the thickness of the first or second wall. Each rib is also preferably at least as wide as it is thick.

A plurality of drain holes is provided through the walls of the tube, preferably in a pattern extending lengthwise along a substantial portion of the length of the tube. At least some of these drain holes are also preferably in line with the parallel ribs so that they either pass through these ribs or are disposed opposite to these ribs or both. The drain holes allow body fluids accumulating in a cavity into which the tube has been introduced to pass into the tube and along the passageway extending lengthwise inside the tube into a disposal device outside the drainage site. The disposal device may include a suction mechanism for applying suction pressure to the tube.

When suction pressure is applied to the tube or when lateral compressive forces are applied by body movements and the healing process, total collapse of the tube is prevented by the internal ribs which impinge against the opposite walls to cause the walls to remain slightly spaced apart. The relatively stocky ribs (referred to as stocky because each rib is at least as wide as it is thick as mentioned above) are not subject to lateral buckling or collapse and thereby prevent collapse of the tube despite very high internal and/or external lateral pressure. The body movements of the patient also tend to cause relative lateral movements of the flat walls of the tube and therefore relative lateral movement of the ribs. These lateral movements of the ribs subject the material in the tube to stresses which prevent the formation of or break up any obstructions which might otherwise form in the tube, for example, as a result of coagulation of the material in the tube.

The drainage tubes of the invention may also be provided with an X-ray opaque stripe, with longitudinally spaced indicia markings, or with both of these features so that the placement and movement of the drain tube in a drainage site can be monitored by X-ray, fluoroscopic, or visual means.

Thus, the object of the invention to maintain a continuous drainage passageway in a soft flexible drainage tube is achieved by providing such a tube which has properties and design characteristics which enable it to take advantage of expected forces caused, for example, by normal body movements of the patient and compressive forces of the healing process and which have otherwise heretofore been found to be inhibiting to a continuous drainage function.

Further features of the invention, its nature and various advantages will be more apparent from the accompanying drawing and the following detailed description of the invention.

BRIEF DESCRIPTION OF THE DRAWING

FIG. 1 is a longitudinal view of a first embodiment of the drainage tube of the invention.

FIG. 2 is a cross sectional view taken along the line 2—2 in FIG. 1.

FIG. 3 is a cross sectional view taken along the line 3—3 in FIG. 1.

FIG. 4 is a cross sectional view taken along the line 4—4 in FIG. 1.

FIG. 5 is a composite cross sectional view similar to FIGS. 3 and 4 showing the tube under compressive forces and subject to relative lateral displacement of the flat side walls of the tube.

FIG. 6 is a view similar to FIG. 5 showing opposite relative lateral displacement of the flat side walls of the tube.

FIG. 7 is a longitudinal view of a second embodiment of the drainage tube of the invention.

FIG. 8 is a cross sectional view taken along the line 8—8 in FIG. 7.

FIG. 9 is a cross sectional view taken along the line 9—9 in FIG. 7.

FIG. 10 is a cross sectional view taken along the line 10—10 in FIG. 7.

FIG. 11 is a composite cross sectional view similar to FIGS. 9 and 10 showing the tube under compressive forces and subject to relative lateral displacement of the flat side walls of the tube.

FIG. 12 is a view similar to FIG. 11 showing opposite relative lateral displacement of the flat side walls of the tube.

DETAILED DESCRIPTION OF THE INVENTION

A first illustrative embodiment of the flexible body fluid drain tube 10 of the invention is shown in FIGS. 1-6. Drain tube 10 has internal passageway 11 for conveying body fluids from the drainage site in which the tube is located to the exterior of the patient. Typically, at least the portion of the tube to the left of mark 32b as viewed in FIG. 1 is located inside the patient and body fluids collected by the tube flow to the right and exit via coupling 13 into a disposal device (not shown) or to another tube (also not shown) leading to a disposal device. Accordingly, the portion of tube 10 to the left as viewed in FIG. 1 is the distal end portion of the tube, and the portion of tube 10 to the right in FIG. 1 is the proximal end portion of the tube. Tube 10 may be made of any suitable soft, flexible, usually rubberlike material, preferably conventional silicone rubber. The term "rubber" or "rubberlike" is used herein and in the appended claims to mean any such material.

As seen in FIGS. 2-4, tube 10 has relatively thin, relatively wide, substantially flat opposite first and second walls 12 and 14 which are spaced apart by a distance substantially less than the width of either wall 12 or 14, and also preferably less than the sum of the thicknesses of rib 20 and either of ribs 16 or 18 as described in detail below. Although the drains of this invention may be made in any of a wide range of sizes, each of the walls 12 and 14 in a typical drain may be about 0.4 inch wide and 0.03 inch thick, and the inside surfaces of walls 12 and 14 may be spaced apart about 0.09 inch in the absence of any compressive forces on the tube. Walls 12 and 14 are joined along their adjacent lateral edges by curved wall portions 22 and 24 to form tube 10. Curved wall portions 22 and 24 are preferably slightly thicker than walls 12 and 4, preferably about 1.5 to 2.5 times thicker than walls 12 and 14, to help keep the drain from collapsing in the corners and to increase its resiliency. For example, if flat walls 12 and 14 are about 0.03 inch thick, curved wall portions 22 and 24 may be about 0.04 or 0.05 inch thick at the thickest region. Because the width of walls 12 and 14 is substantially greater than the distance between them, tube 10 has a substantially flat cross section and is sometimes referred to herein as a flat tube.

A pair of parallel ribs 16 and 18 extend longitudinally of tube 10 internally of first wall 12, and a single internal rib 20 extends longitudinally of tube 10 internally of second wall 14. All of ribs 16, 18, and 20 are typically made of the same material as the walls of tube 10, and are preferably integral with the tube and formed at the same time as the tube is formed. Each of ribs 16, 18, and 20 is substantially wider (measured parallel to walls 12 and 14) and thicker (measured perpendicular to walls 12 and 14) than the thickness of either of walls 12 and 14. Preferably the width and thickness of each rib is in the range from about 2 to 4 times the thickness of wall 12 or 14. In addition, each rib is at least as wide as it is thick, and preferably wider than it is thick. Rib 20 is also preferably a main rib with width and thickness respectively greater than the width and thickness of ribs 16 and 18. For example, in a tube in which flat walls 12 and 14 are about 0.03 inch thick, each of ribs 16 and 18 is preferably about 0.075 inch wide and 0.06 inch thick, and rib 20 is preferably about 0.09 inch wide and 0.07 inch thick. Accordingly, all of ribs 16, 18, and 20 are relatively prominent (because they are at least twice as thick as the flat walls of the tube) but stocky (because they are at least as wide as they are thick). These ribs are therefore relatively firm and resist both lateral compression and lateral buckling, i.e., they will not collapse or fold over on themselves laterally when the tube is subjected to lateral compressive forces as described in greater detail below. On the other hand, ribs 16, 18, and 20 are not so massive that they substantially interfere with the longitudinal flexibility and suppleness of the tube.

Ribs 16 and 18 are laterally spaced apart from each other by a distance greater than the width of rib 20, preferably about 1.5 to 2.5 times the width of rib 20. The spacing between ribs 16 and 18 is also preferably greater than the distance between each rib and the adjacent lateral edge of the wall 12 to which ribs 16 and 18 are connected. For example, if the width of wall 12 is about 0.4 inch, the width of rib 20 is about 0.09 inch, and the width of each of ribs 16 and 18 is about 0.075 inch, then the spacing between each of ribs 16 and 18 and the adjacent lateral edge of wall 12 may be about 0.06 inch. Rib 20 is (at least initially) preferably located midway between ribs 16 and 18.

As is apparent from the drawing and the illustrative dimensions mentioned above, the projection of rib 20 into the interior of tube 10 preferably overlaps the projection of ribs 16 and 18 into the interior of the tube even when the tube is not subject to any lateral compressive forces. Rib 20 will therefore contact one of ribs 16 and 18 when walls 12 and 14 are subjected to sufficient relative lateral displacement as described in more detail below.

A pattern of drain holes 26 and 28 through both walls 12 and 14 extends lengthwise in two parallel lines along a substantial portion of the length of tube 10. In the embodiment shown in FIGS. 1-6, holes 26 and 28 are stamped straight through both walls 12 and 14. Holes 26 are indicated as 26a through wall 14, and as 26b through wall 12. Similarly, holes 28 are indicated as 28a through wall 14, and as 28b through wall 12. In the preferred embodiment shown in FIGS. 1-6, holes 26 and 28 are larger in diameter than the width of ribs 16 and 18. Also in this embodiment the lines of holes are arranged so that holes 26b and 28b extend through ribs 16 and 18, thus interrupting those ribs where the holes occur.

while holes 26a and 28a are located opposite the axes of ribs 16 and 18.

Tube 10 may have visible indicia marks 32a, 32b, 32c, and 32d as seen in FIG. 1, and an X-ray opaque stripe 34 down its center line as seen in FIGS. 1-6 for monitoring and inspecting the application, use, and withdrawal of the device by X-ray, fluoroscopic, and/or visual means. For example, visible mark 32a is near the distal end of tube 10. When tube 10 is withdrawn from the patient, the physician knows that the entire tube has been recovered intact if he finds mark 32a near the distal end of the tube. The closely spaced pair of marks 32c and 32d visually inform the physician that the proximal end of the pattern of holes 26, 28 is a first predetermined distance from those marks, and the single mark 32b similarly provides visual information that the proximal end of the pattern of holes is a second shorter distance from that mark.

In use, ribs 16, 18, and 20 prevent complete collapse of tube 10 even when the tube is subjected to lateral compressive forces due to suction pressure which may be applied to the tube, or due to the patient's body movements and the healing process. In FIGS. 5 and 6 these compressive forces are represented by arrows 21. Ribs 16, 18, and 20 hold walls 12 and 14 apart by bearing against the opposite portions of the walls, thereby keeping the drainage passageway open. The tubes of this invention are capable of withstanding very strong internal and/or external forces. For example, these tubes do not completely collapse even when subjected to suction pressures as high as 26 inches of mercury. They can thus be used with the highest regulated or unregulated vacuums generally available in hospitals. The flat shape of the tubes, as well as their softness, flexibility, and resistance to collapse make them especially suitable for use in drainage sites in soft tissue such as in head, neck, and breast surgery where the use of a relatively high vacuum in the drain is desirable not only for good drainage but also to hold the tissues together to promote healing. These same characteristics make the drains of this invention suitable for flap surgery of any kind where again a high vacuum in the drain is used to help keep the adjacent tissues together during healing.

In addition to preventing tube 10 from collapsing, ribs 16, 18, and 20 help to keep holes 26 and 28 and passageway 11 clear of obstructions resulting, for example, from coagulation of the body fluids being drained. As tube 10 is distorted by body movements and the healing process, walls 12 and 14 tend to be subjected to relative lateral displacements between the two extreme positions shown respectively in FIGS. 5 and 6. In the first of these positions, ribs 16 and 20 contact one another as shown in FIG. 5. In the second position, ribs 18 and 20 contact one another as shown in FIG. 6. Between these extreme positions, rib 20 tends to wipe the inside surface of wall 12 between ribs 16 and 18. As a result of the relative lateral motions of the various parts of tube 10, especially the lateral motion of rib 20 relative to ribs 16 and 18, the material in passageway 11 is subjected to various transverse forces which squeeze, knead, roll, or otherwise work that material to prevent the formation of obstructions in the tube or to break down any such obstructions which may have formed. These same transverse working forces also help to keep holes 26 and 28 clear. The prominence and stockiness of the ribs assures that the material in the tube is worked effectively by the relative lateral motions of the ribs.

The body movements and healing process which cause the above-described relative lateral motions of walls 12 and 14 may be slow and intermittent, but the patient will usually be encouraged by the surgeon to move around somewhat in order to expedite the process. It has been found in practice that any solid, semisolid, or gelatinous material coming into the tube or forming in the tube will be prevented from obstructing either holes 26 and 28 or passageway 11 by the transverse forces exerted on the material in the tube as a result of the relative lateral motions of the various features of the tube, and particularly the lateral motions of the ribs relative to one another and to the walls of the tube. In this way tube 10 is kept sufficiently clear to maintain the drainage function.

An alternative embodiment of the drain tube of this invention is shown in FIGS. 7-12. Drain tube 40 in this embodiment may be basically similar to drain tube 10 in the first embodiment described above. Tube 40 has relatively thin, relatively wide, substantially flat, opposite first and second walls 42 and 44 spaced apart as described above and joined along their adjacent lateral edges at 50 and 52 to define internal passageway 41. A pair of parallel ribs 46 and 48 (similar to ribs 16 and 18 in the first embodiment) extend longitudinally of the tube internally of wall 42. A single internal rib 54 (similar to rib 20 in the first embodiment) extends longitudinally of wall 44 and along the center line of that wall substantially midway between ribs 46 and 48. The relative sizes, shapes, and locations of ribs 46, 48, and 54 are all similar to the corresponding ribs in the first embodiment. Drain holes 56 and 58 are provided through wall 44 in two parallel lines extending longitudinally along a substantial portion of the length of tube 40. As seen in FIG. 9, holes 56 and 58 are disposed opposite to and in line with ribs 46 and 48, but unlike the first embodiment no holes extend through ribs 46 and 48. A third line of holes 60 is provided through wall 42 opposite to and in line with rib 54. All of holes 56, 58, and 60 are preferably wider than the opposite ribs so that the ribs will not block the holes when the tube is subjected to lateral compressive forces.

Tube 40 may have visible indicia marks 66a, 66b, 66c, and 66d (similar to marks 32a-d in the first embodiment) and X-ray opaque stripe 68 (similar to stripe 34 in the first embodiment) for the same purposes described in connection with the first embodiment.

Operation of drain tube 40, illustrated in FIGS. 11 and 12, is basically similar to operation of drain tube 10 described above. Again, ribs 46, 48, and 54 prevent the tube from collapsing when subjected to lateral compressive forces. And again, relative lateral motion of walls 42 and 44, and hence lateral motion of rib 54 relative to ribs 46 and 48, subjects the material in passageway 41 to transverse forces which prevent the formation of any obstructions in passageway 41 or break up any obstructions which may have formed, thereby keeping passageway 41 clear. In this embodiment, however, each line of holes 56, 58, and 60 is more directly subject to the wiping action of one of ribs 46, 48, and 54 as walls 42 and 44 move laterally relative to one another. This wiping action of the ribs relative to the holes helps to keep all of the holes free of any obstructions.

From the foregoing it will be apparent that the drainage tubes of this invention make use of compressive forces and movements, which were previously considered as inhibiting the drainage function, to help keep the drainage passageway open.

It will be understood that the embodiments shown and described herein are only illustrative of the principles of the invention, and that various modifications can be implemented by those skilled in the art without departing from the scope and spirit of the invention. For example, the drainage holes can be arranged in any of a wide variety of patterns.

We claim:

1. A substantially flat drain for use in draining body fluids from a surgically created drainage site in the body comprising:
    a longitudinal flexible rubber tube having first and second opposite, mutually parallel, substantially flat walls spaced apart by a distance subtantially less than the width of the flat walls and joined along their adjacent lateral edges;
    a plurality of holes through each of the flat walls of the tube for admitting body fluids from the drainage site into the tube for conveying from the drainage site via the tube;
    first and second laterally spaced, mutually parallel, longitudinal flexible rubber ribs extending parallel to the longitudinal axis of the tube on the inside of the first flat wall and projecting into the interior of the tube, the width of each of the first and second ribs measured perpendicular to the longitudinal axis of the tube and parallel to the flat walls being at least as great as the projection of the rib from the first flat wall; and
    a third longitudinal flexible rubber rib extending parallel to the longitudinal axis of the tube on the inside of the second flat wall and projecting into the interior of the tube intermediate the first and second ribs, the width of the third rib measured perpendicular to the longitudinal axis of the tube and parallel to the flat walls being at least as great as the projection of the third rib from the second flat wall, the first and second ribs being laterally spaced by a distance greater than the width of the third rib and the third rib projecting at least partially into the space between the first and second ribs even when the tube is unstressed, the ribs preventing the flat walls from contacting one another and occluding the tube when the tube is subjected to compression forces perpendicular to the flat walls, and the ribs cooperating with one another and with the walls of the tube to break up any obstructions which may tend to form in the tube by subjecting the material in the tube to transverse forces when the flat walls of the tube are subjected to relative lateral displacements by movements of the body surrounding the drainage site.

2. The drain defined in claim 1 wherein the width and thickness of each rib is at least twice the thickness of the flat walls of the tube.

3. The drain defined in claim 2 wherein the width and thickness of each rib is in the range from 2 to 4 times the thickness of the flat walls of the tube.

4. The drain defined in claim 3 wherein the first and second ribs are laterally spaced by a distance in the range from 1.5 to 2.5 times the width of the third rib.

5. The drain defined in claim 4 wherein the flat walls of the tube are joined along their adjacent lateral edges by wall portions having thickness in the range from 1.5 to 2.5 times the thickness of the flat walls.

6. The drain defined in claim 4 wherein the third rib has width and thickness respectively greater than the width and thickness of the first and second ribs.

7. The drain defined in claim 1 wherein the holes are formed in pairs through opposite portions of the first and second flat walls of the tube.

8. The drain defined in claim 7 wherein each hole through the first flat wall of the tube extends through and interrupts one of the first and second ribs.

9. The drain defined in claim 1 wherein each hole is formed through one of the the flat walls of the tube opposite one of the ribs.

* * * * *